United States Patent
Lenzi et al.

(10) Patent No.: US 12,290,455 B2
(45) Date of Patent: May 6, 2025

(54) SEMI-ACTIVE ANKLE AND FOOT PROSTHESIS POWERED BY A LOCKABLE SERIES-ELASTIC ACTUATOR

(71) Applicant: UNIVERSITY OF UTAH RESEARCH FOUNDATION, Salt Lake City, UT (US)

(72) Inventors: Tommaso Lenzi, Salt Lake City, UT (US); Lukas R. Gabert, Salt Lake City, UT (US); Connelly Ray Buchanan, Salt Lake City, UT (US); Samuel Westgard, Salt Lake City, UT (US); Minh Tran, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 18/797,168

(22) Filed: Aug. 7, 2024

(65) Prior Publication Data
US 2024/0398590 A1 Dec. 5, 2024

Related U.S. Application Data

(63) Continuation of application No. PCT/US2023/017845, filed on Apr. 7, 2023.
(Continued)

(51) Int. Cl.
*A61F 2/66* (2006.01)
*A61F 2/70* (2006.01)
(Continued)

(52) U.S. Cl.
CPC .... *A61F 2/6607* (2013.01); *A61F 2002/5007* (2013.01); *A61F 2002/5033* (2013.01);
(Continued)

(58) Field of Classification Search
None
See application file for complete search history.

(56) References Cited

U.S. PATENT DOCUMENTS

| 8,512,415 B2 | 8/2013 | Herr et al. |
| 10,543,109 B2 | 1/2020 | Holgate |

(Continued)

FOREIGN PATENT DOCUMENTS

| CN | 103006357 | 4/2013 |
| CN | 107349036 | 11/2017 |

(Continued)

OTHER PUBLICATIONS

Bellman et al., SPARKy 3: Design of an Active Robotic Ankle Prosthesis with Two Actuated Degrees of Freedom Using Regenerative Kinetics, IEEE, 2008, https://www.researchgate.net/profile/Ryan-Bellman/publication/224376142_SPARKy_3_Design_of_an_active_robotic_ankle_prosthesis_with_two_actuated_degrees_of_freedom_using_regenerative_kinetics/links/5875415d08ae6eb871c9b5bf/SPARKy-3-Design-of-an-active-robotic-ankle-prosthesis-with-two-actuated-degrees-of-freedom-using-regenerative-kinetics.pdf (Accessed Oct. 13, 2022).

(Continued)

*Primary Examiner* — David H Willse
(74) *Attorney, Agent, or Firm* — Thorpe North & Western, LLP

(57) ABSTRACT

A semi-powered foot and ankle prosthesis (100) has a foot member (128) coupled to the ankle frame (112) and movable with respect to the ankle frame (112). A linear actuator (144) is coupled to and between the ankle frame (112) and the foot member (128) to move the foot member (128) with respect to the ankle frame (112). The linear actuator (144) has a drive motor (150). A locking mechanism (104) selectively engages the drive motor (150) to selectively lock movement (Continued)

of the drive motor (150) to resist a force on the foot member (128) from backdriving the linear actuator (144).

27 Claims, 9 Drawing Sheets

Related U.S. Application Data

(60) Provisional application No. 63/328,646, filed on Apr. 7, 2022.

(51) Int. Cl.
    *A61F 2/50*         (2006.01)
    *A61F 2/68*         (2006.01)

(52) U.S. Cl.
    CPC ............... *A61F 2002/6614* (2013.01); *A61F 2002/6621* (2013.01); *A61F 2002/6818* (2013.01); *A61F 2002/6836* (2013.01); *A61F 2002/6854* (2013.01); *A61F 2002/701* (2013.01)

(56) References Cited

U.S. PATENT DOCUMENTS

| | | |
|---|---|---|
| 10,772,742 B2 | 9/2020 | Lenzi et al. |
| 11,147,693 B2 | 10/2021 | Kim et al. |
| 11,273,060 B2 | 3/2022 | Herr et al. |
| 11,285,024 B2 | 3/2022 | Clausen |
| 2022/0160522 A1* | 5/2022 | Herr ............... A61F 2/6607 |

FOREIGN PATENT DOCUMENTS

| | | |
|---|---|---|
| CN | 110074905 | 8/2019 |
| CN | 111437082 | 7/2020 |

OTHER PUBLICATIONS

Grimmer et al., A powered prosthetic ankle joint for walking and running, BioMed Eng OnLine, 15(Suppl 3):141, 2016, 16 pages, https://link.springer.com/content/pdf/10.1186/s12938-016-0286-7.pdf (Accessed Oct. 13, 2022).

Xu et al., Design of bionic active-passive hybrid-driven prosthesis based on gait analysis and simulation of compound control method, BioMedical Engineering OnLine, 20:126, 2021, 20 pages, https://biomedical-engineering-online.biomedcentral.com/counter/pdf/10.1186/s12938-021-00962-9.pdf (Accessed Oct. 13, 2022).

Yu et al., The design, control and testing of anintegrated electrohydrostatic powered ankle prosthesis, IEEE/ASME Transactions onMechatronics, vol. 24, No. 3, 2019, pp. 1011-1022, https://purehost.bath.ac.uk/ws/files/201410841/Author_Revision.pdf(Accessed Oct. 13, 2022).

\* cited by examiner

SEMI-ACTIVE ANKLE AND FOOT PROSTHESIS POWERED BY A LOCKABLE SERIES-ELASTIC ACTUATOR

CROSS REFERENCE TO RELATED APPLICATIONS

This application is a continuation application of PCT International Application No. PCT/US2023/017845, filed Apr. 7, 2023 which claims priority to U.S. Provisional Patent Application No. 63/328,646, filed Apr. 7, 2022, which are each incorporated herein by reference.

STATEMENT REGARDING FEDERALLY SPONSORED RESEARCH OR DEVELOPMENT

This invention was made with government support under W81XWH21-1-0037 awarded by the DOD/USAMRDC, and HD098154 awarded by the National Institutes of Health. The government has certain rights in the invention.

NAMES OF THE PARTIES TO A JOINT RESEARCH AGREEMENT

Not applicable.

INCORPORATION BY REFERENCE STATEMENT

International Application Number PCT/US2022/022374, filed Mar. 29, 2022, and published as WO 2022/212397, and which claims priority to U.S. Provisional Patent Application No. 63/168,128, filed Mar. 30, 2021, is incorporated herein by reference.

BACKGROUND

The quality of life and ambulation ability of over one million people is affected by lower limb amputation in the United States. Currently available passive prostheses use springs and dampers to provide torque at the joint level. These prostheses can be reliable and lightweight; however, they may not inject net positive energy into the gait cycle. This makes many ambulation activities difficult to perform and consequently contributes to compensatory ambulation movements which can negatively affect long term health. Fully powered prostheses have been developed that can inject net positive energy into the gait cycle. However, because some ambulation activities require high speed and others require high torque, powering all ambulation activities often leads to heavier prostheses. Fully powered prostheses also rely on battery power, potentially limiting amputee independence. The development of lower limb prostheses is an ongoing endeavor.

SUMMARY

This invention relates to a compact and lightweight semi-active ankle foot prosthesis powered by a lockable series-elastic actuator. An ankle frame is configured to be coupled to a connector. A foot member is coupled to the ankle frame and movable with respect to the ankle frame. A linear actuator is coupled to and between the ankle frame and the foot member. The linear actuator moves the foot member with respect to the ankle frame. The linear actuator has a drive motor. A locking mechanism selectively engages the drive motor to selectively lock movement of the drive motor to resist a force on the foot member from backdriving the linear actuator.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 1b is a partial front perspective view of the foot and ankle prosthesis of FIG. 1a.

FIG. 1c is a partial rear perspective view of the foot and ankle prosthesis of FIG. 1a.

FIG. 2b is a partial cross-sectional side view of the foot and ankle prosthesis of FIG. 1a.

FIG. 3 is a schematic illustration of the foot and ankle prosthesis of FIG. 1a.

FIG. 4 is a rear view of the foot and ankle prosthesis of FIG. 1a.

FIG. 5c is a partial detailed perspective view of the locking mechanism of the foot and ankle prosthesis of FIG. 1a.

FIG. 7 is a schematic illustration of the locking mechanism of FIG. 5a.

Figure 1A:
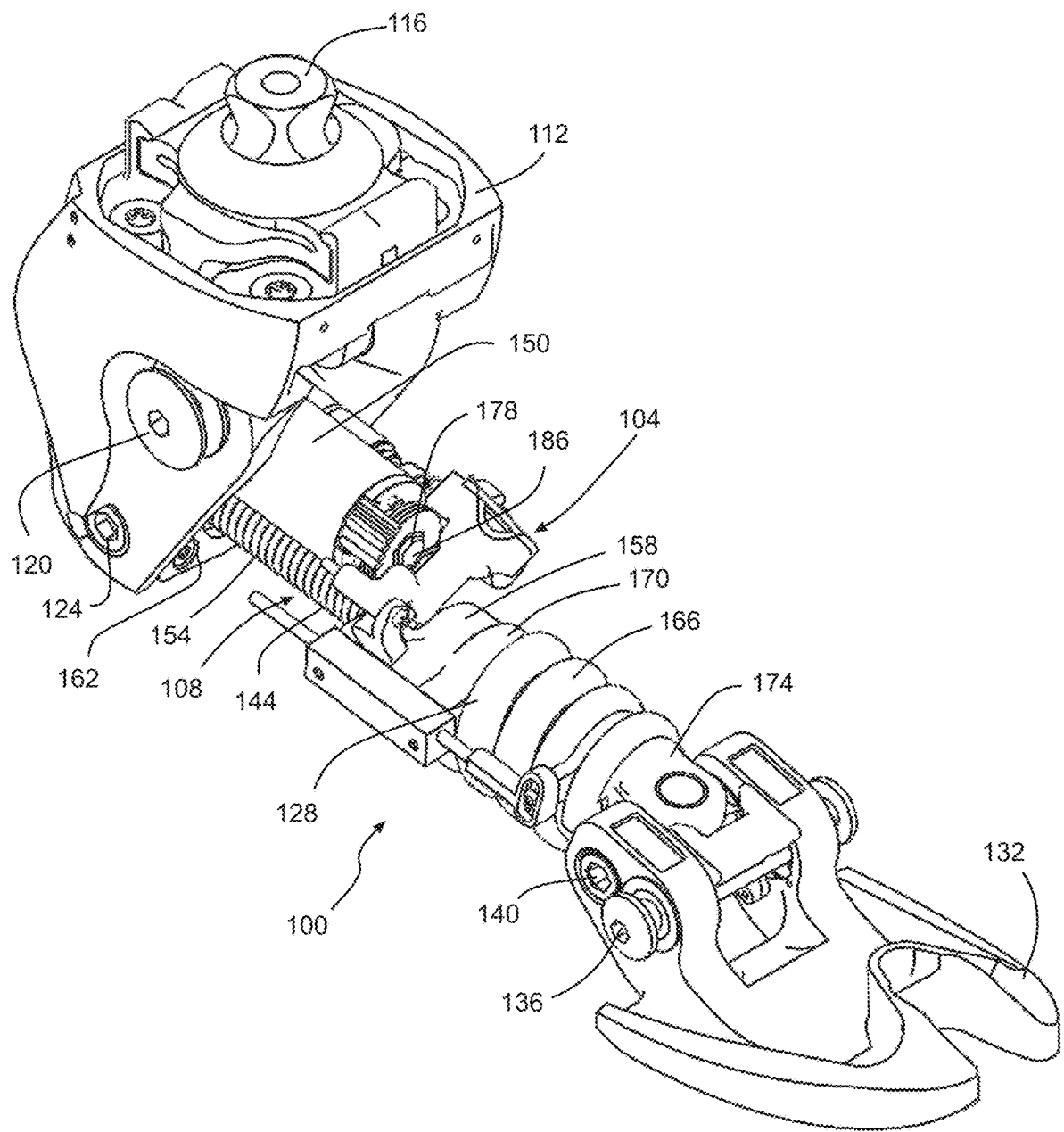
FIG. 1a is a partial front perspective view of a semi-powered foot and ankle prosthesis powered by a lockable series-elastic actuator in accordance with one example, shown with a foot shell removed for visibility.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a spring" includes reference to one or more of such features and reference to "the electrode" refers to one or more of such electrodes.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, or combinations of each.

Numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

The terms "interference fit" and "friction fit" are terms of art used interchangeably herein to refer to deliberately causing, increasing and/or using friction to deliberately resist movement. An interference fit or friction fit is different than and great than the existence of friction. While friction may exist between any two surfaces, it is often desirable to do all one can to reduce this friction. An interference fit or friction fit can be distinguished from naturally occurring friction by being actually deliberately caused and increased. An interference fit can be created by dimensioning engaging parts so that their surfaces tightly bear against one another. A friction fit can be created by surface roughness that is rougher.

A prismatic joint is a one-degree-of-freedom kinematic pair which constrains the motion of two bodies to sliding along a common axis, without rotation.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

EXAMPLE EMBODIMENTS

A technology is described for a compact and lightweight semi-active and semi-powered ankle foot prosthesis powered by a lockable series-elastic actuator. The semi-active ankle foot prosthesis can include two main subsystems, namely, a main drivetrain with an integrated series-elastic actuator, and a locking mechanism for selecting between an active or powered mode and a passive mode. The semi-active prosthesis is a hybrid of passive and powered prostheses that can selectively power lower torque ambulation activities while relying on passive performance for high torque activities. Thus, the semi-active prosthesis can be small and lightweight, while still being able to inject net positive energy into the gait cycle for some ambulation activities.

In 2005, one in 190 Americans were living with the loss of a limb, which equates to 1.6 million people in the United States. Projections estimate that number will likely double to 3.6 million by 2050. Of the 1.6 million, one million were lower limb amputees. This increase in amputations is largely due to the increase in peripheral vascular disease. Amputation can affect the quality of life of the individual. Amputation can also affect mobility of the individual. For example, the average able-bodied individual walks 5100 steps per day. Whereas the average amputee walks only 3000 steps per day. Amputees with a transtibial or below knee amputation spend more energy than able bodied individuals and still walk slower than able-bodied individuals. Below knee amputations also make it more difficult to do other activities besides walk, such as climb stairs and ramps, and stand up from a sitting position.

Some ankle prostheses have been developed attempting to restore mobility post amputation. Today the most commercially available protheses are passive prosthetics. The most fundamental version of a passive prosthesis is a simple stiffness element often made up of a carbon fiber spring. These carbon fiber foot keels can be extremely lightweight. However, they can also have a fixed equilibrium position that is tuned for more common level ground ambulation activities, such as walking and standing. This can pose a problem for ambulation activities like stairs, ramps, and sit-to-stand transitions, because they require greater ranges of motion. Using a stiffness element prosthesis on inclined terrain can create increased instability due to a lack of range of motion.

A newer category of passive prosthesis can employ a joint with passive elements like springs and dampers. Microprocessor ankles use a microprocessor to tune the dampers according to onboard sensors. These types of devices, however, can neglect that during the push-off phase of ambulation, the ankle provides net positive energy. They can also be incapable of actively positioning the joint during the swing. For example, positioning the ankle during swing in stair ascent for toe clearance reduces the likelihood of tripping. Positioning in-swing can also aid in adapting to inclined terrain. Because passive devices can be energetically passive, they may not actively control these movements. This can often lead to the employment of unnatural compensatory movements to compensate for the lack of net positive energy. For example, on stairs, amputees often cannot ascend step-over-step like able bodied individuals. Rather, they ascend one step at a time, taking each step with their intact limb first. To clear the steps, the amputee also may extend and circumduct in an unnatural way.

Fully powered prosthetics can provide net positive energy where passive prosthetics may not. These fully powered prosthetics can employ batteries, motors, and clever transmission systems to provide power at the ankle joint. As the name implies, these devices may rely on their active components to power all ambulation activities. These devices may actively provide push-off and actively control swing. This ability may lead to an amputee being able to perform stairs in a step-over-step fashion. However, because some ambulation activities require high torque, and some ambulation activities require high speed, powering all ambulation activities often leads to demanding motor requirements. The added components, like heavy motors, large batteries, and bulky transmission components may lead to heavier fully-powered prostheses. Increasing weight may be a problem because increasing prosthetic weight may lead to increased metabolic cost.

The semi-active prosthesis can secure the benefits of both passive prostheses and fully powered prostheses, while avoiding some of the inherent pitfalls of both. Some semi-active prostheses achieve this by using low power actuators to power the prosthesis during low load activities, like swing. These types of prostheses maintain some of the benefits of active repositioning in swing that fully powered devices have, like improving toe clearance to reduce falls, while maintaining a relatively light overall weight. While devices of this category may be able to reposition in swing, they can give up any net positive energy injection during stance. Another way semi-active prostheses may maintain net positive energy injection and swing repositioning while still preserving a lightweight constitution is by selectively powering a subset of ambulation activities.

Therefore, technology is described for a semi-active ankle and foot prosthesis powered by a lockable series clastic actuator. The device can be an ankle and foot prosthesis because it can have both an ankle joint and a toe joint. Toe joint stiffness can have a significant effect on push-off work during walking. The semi-active prosthesis can selectively power a subset of ambulation activities. The semi-active prosthesis can maintain a very low build height, size, and weight. The low build height can make the device usable for the amputee population with longer residual limbs. The compact size and weight of the prosthesis can be enabled through use of a locking mechanism that can lock a dual-function, series-elastic actuator during passive activities, and unlock the series-elastic actuator during powered activities. During the passive mode, the main drive motor can be completely powered off. The passive function of the prosthesis can be founded on the use of a passive spring. The powered function of the prosthesis can use an electrical motor, transmission system, and 4-bar linkage.

The series-clastic actuator can utilize a ball screw. When driven by the motor, the series-elastic actuator can apply torque at the joint level. In passive mode, the motor can be turned off, and thus may not provide movement to the ball screw. If the ball screw has no resistance during stance phase, the ankle joint can move, and the prosthesis may collapse under the weight of the user. Thus, the locking mechanism that can stop the ball screw from moving, and can enable the prosthesis to function in passive mode.

The locking mechanism can prevent and resist the ball screw from being backdriven. Backdriving the ball screw can require backdriving the entire main drivetrain (drive motor and gearbox). Consequently, preventing and resisting the main drivetrain motor from being backdriven, can also prevent and resist the ball screw from being backdriven. Thus, the locking mechanism can prevent and resist the main motor from backdriving, and can take advantage of the main drivetrain's transmission ratio to significantly reduce the required holding torque of the locking mechanism. As load may positively correlate with size and weight, reducing the braking load can help to reduce the size and weight of the locking mechanism.

The locking mechanism can lock or unlock the main motor under speed and torque. Locking or unlocking the main motor under load can make the prosthesis capable of transitioning between active and passive modes without requiring the user to pause or wait for the lock to engage, thus applying a damping torque. This attribute can also make the prosthesis more robust. For example, if the locking mechanism is triggered inadvertently, it is less likely to be damaged by shock loading when locking under speed.

In addition, the locking mechanism can be locked in two directions. Locking in two directions can allow the locking mechanism to stay locked when there is a compression or extension load on the passive spring. As both dorsiflexion and plantarflexion torque can be present in the stance portion of the gait cycle, there can be both tension and compression loads on the passive spring. Thus, the compression and extension loads may become an issue if the locking mechanism can only be locked in one direction. In that scenario, the ball screw might stay locked during ankle dorsiflexion torque, but then unlock under ankle plantarflexion torque.

In addition, the locking mechanism can remain locked even with a lack of power, or without continuous power consumption. "Power on brake on" type brakes may use permanent magnets or springs to force two friction materials out of contact when power is off. When power is applied to the brake, an electromagnet overcomes the spring force putting the friction materials back into contact. "Power off brake on" type brakes may work on similar principles, but in reverse. The power consumption required for "power on brake on" type brakes may make the passive function of the device less energy efficient, and may make ambulating with a dead battery impossible. "Power off brake on" type brakes may enable ambulation on a dead battery, but may make the active mode of ambulation less energy efficient. The present locking mechanism may not require power in either the on or off state, and may only require power to transition between states.

The locking mechanism has a small size and weight. The prosthesis can have geometrical constraints. Namely, as the ankle flexes into dorsiflexion, the front of the main drive motor can swing towards the back of the prosthesis. Conversely, as the ankle flexes into plantar flexion, the back of the main drive motor can swing towards a top of the foot shell. To minimize the rear dimension of the ankle and enable the ankle to fit into a foot shell and unmodified shoe, the main drive motor can be located in the foot shell and to nearly touch the top of the foot shell when flexed into full plantarflexion. Doing so reduces the rear dimension of the ankle when flexed into dorsiflexion, avoiding large unnatural bulges in the rear portion of the ankle cover. This can help the ankle appear more natural. To prevent increasing the rear dimension of the prosthesis any further by adding a locking mechanism to the front side of the main drive motor, the locking mechanism can attach to the rear part of drive shaft of the main drive motor. The locking mechanism can have a rotor carried by the rear of the drive shaft and engaged by a caliper or brake pads.

The prosthesis may also have non-backdrivable gearing coupled with the rotor and brake pads of the locking mechanism. As described herein, a non-backdrivable gearing mechanism may also be used in the main drivetrain between the main drive motor and the output joint to the ball screw. However, implementing the non-backdrivable gearing mechanism in this way may decrease the efficiency of the main drivetrain, which may lower the efficiency of the prosthesis' active mode. This configuration may also prevent the prosthesis from taking advantage of some of the benefits of backdrivability. One common benefit of having a backdrivable drivetrain is the ability to adapt to uneven terrain. To preserve this benefit and avoid decreasing the efficiency of the main drivetrain, the prosthesis can have the non-backdrivable mechanism as part of the locking mechanism, separate from the main drivetrain. The non-backdrivable gearing mechanism can be positioned in between a brake motor and the rear drive shaft of the main drive motor. However, placing the non-backdrivable gearing between a brake motor and the main drive motor might render the main drive motor locked all the time unless the brake motor was spinning with the drive motor. Placing the locking mechanism in between the non-backdrivable gearing and the rear shaft of the main drive motor can regulate the transmitted torque to the rear shaft of the main drive motor. This allows the locking mechanism to apply no torque, or a continuous range of torques, to the rear drive shaft of the main drive motor. It also allows the main drivetrain to operate without the frictional and inertial losses of a non-backdrivable mechanism.

The locking mechanism can also have a cam style mechanism followed by the rotor and brake pad mechanism to regulate the transmitted torque. The cam mechanism can convert the rotational torque of the cam into linear force on the brake pad. The cam can maintain contact with the brake pad. As the cam rotates, the cam can maintain contact with the brake pad to push it in a linear motion towards the rotor. The rotor can be mounted to the rear end of the drive shaft of the main drive motor. The linear force of the brake pad can be applied to the rotor. When the brake pads contact the rotor, the normal force on the brake pad can regulate the frictional force of the brake pad on the rotor to create a braking torque to the drive shaft of the main drive motor.

A compact planetary gearbox can be positioned before the non-backdrivable gearing mechanism to further decrease the size and required output torque of the brake motor. The non-backdrivable gearing can include leadscrews, worm drives, and other shear friction-based mechanisms. A worm drive can provide an extremely high transmission ratio in a compact single stage in a restrictive space. In addition, the worm drive can be a right-angle transmission system with an offset between the input and output shaft axis. Using a right-angle transmission system with an offset can occupy little of the limited space behind the main drive motor, and can allow a small brake motor parallel to the main motor to drive the lock mechanism in a hollow of the foot shell and between the main drive motor and the ball screw. The brake motor can be positioned lower than the main drive motor where there is more space in the hollow of the foot shell due to the cylindrical geometry of the main drive motor and brake motor.

The locking mechanism can be an actively controlled, friction-based locking mechanism with the ability to lock in two directions, be locked and unlocked under load and speed, have adjustable locking torque, require no continuous power consumption, have infinite locking positions, and be compact and lightweight.

Example 1

Figure 1B:
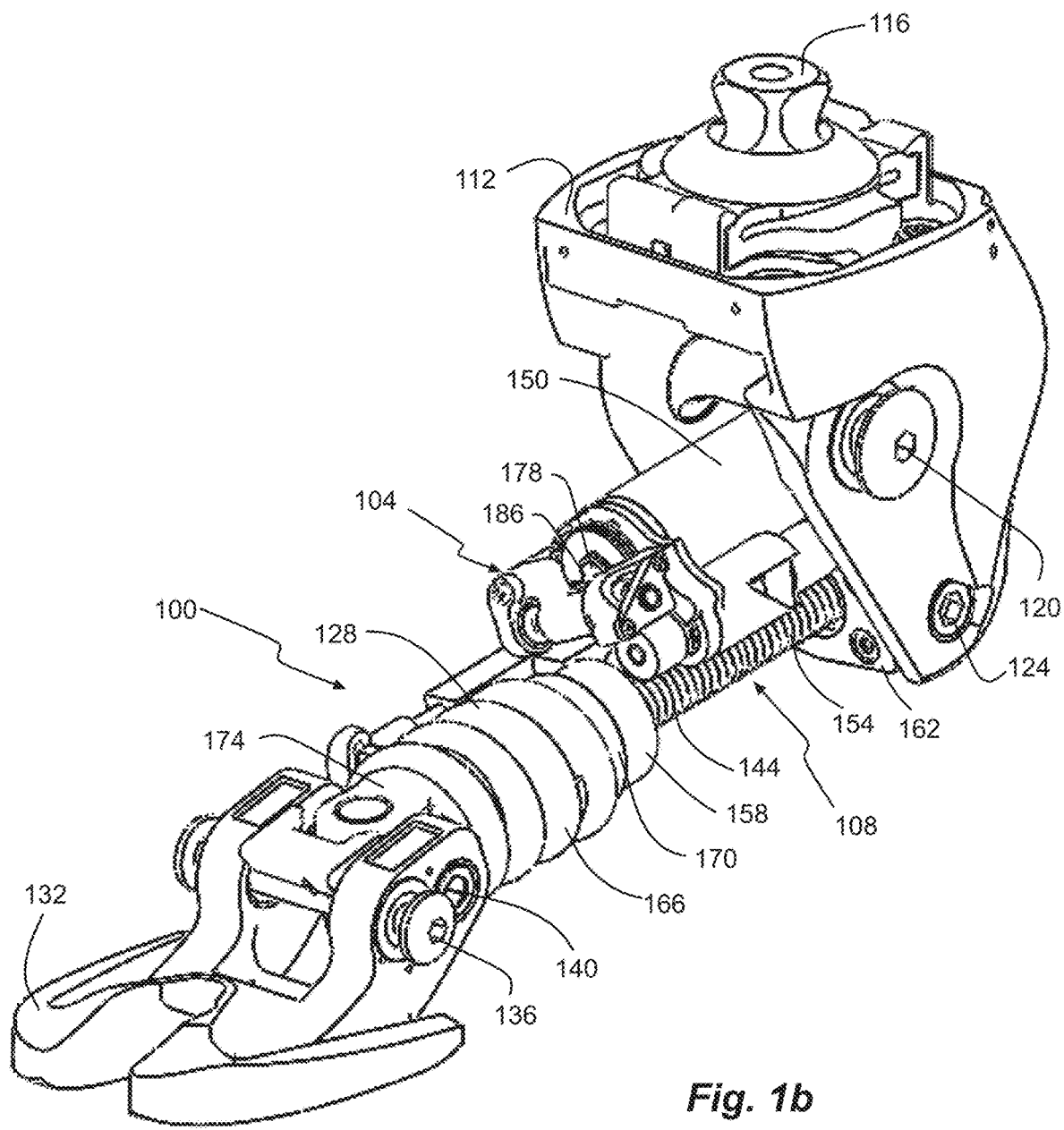
Figure 1C:
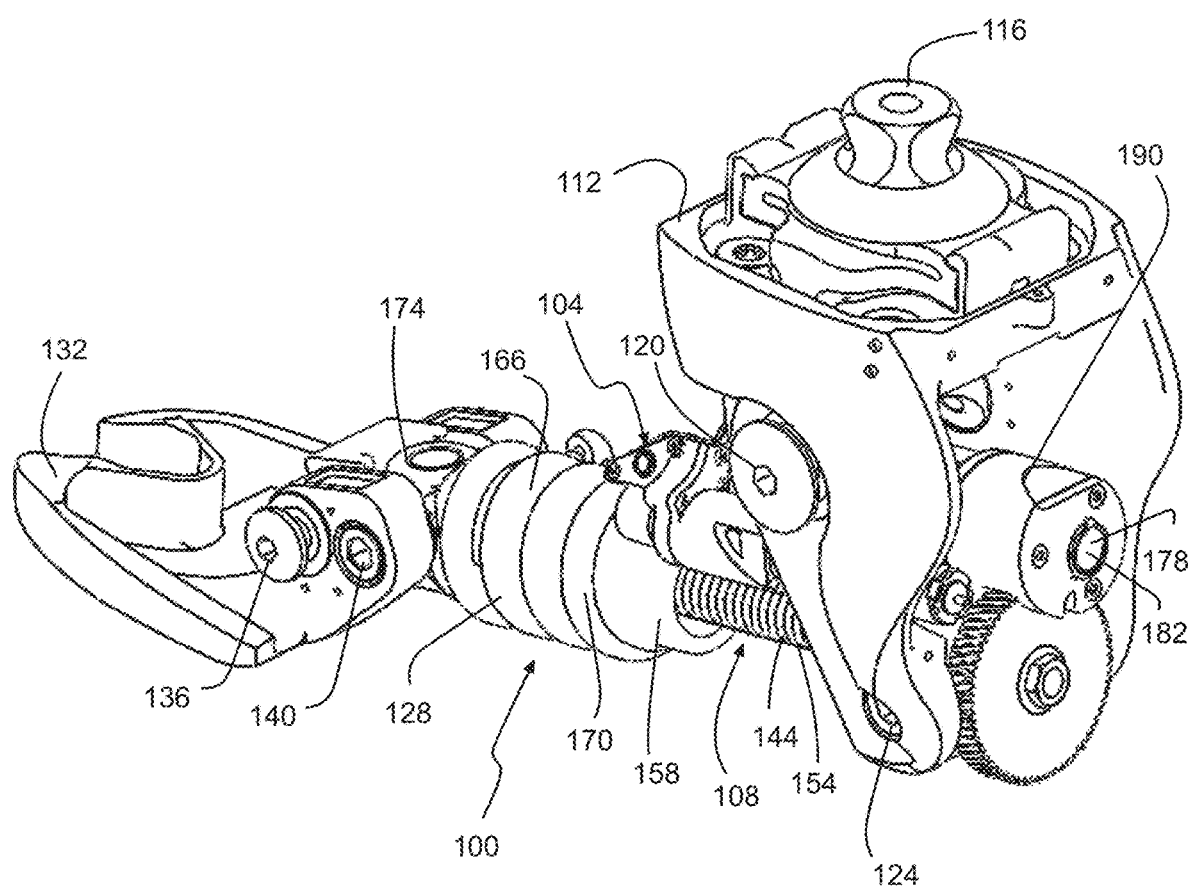

FIGS. 1a-c illustrate a foot and ankle prosthesis 100 with a locking mechanism 104 in one example of the invention. The prosthesis 100 can be semi-powered or semi-active. The prosthesis 100 can be powered by a series-elastic actuator 108. The series-elastic actuator 108 can selectively power lower torque ambulation activities while relying on passive performance for high torque activities. The locking mechanism 104 can select between a powered or active mode and a passive mode.

The prosthesis 100 can have an ankle frame 112. The ankle frame 112 can be positioned at a location corresponding to an ankle of a natural foot. The ankle frame 112 can be coupled to a connector 116. In one aspect, the connector 116 can be a pyramid adaptor that can be attached to a pylon (not shown) or socket (not shown) to receive a remnant limb of an amputee. The ankle frame 112 can have at least one revolute joint to act as the ankle of the natural foot. In one aspect, the ankle frame can have an ankle joint 120 and a first joint 124 positioned below the ankle joint 120. In one aspect, the ankle frame 112 can be formed of metal, such as aluminum, and can be formed by machining or casting.

A foot member 128 can be coupled to the ankle frame 112 and movable with respect to the ankle frame 112. In one aspect, the foot member 128 can comprise a toe frame 132 spaced-apart from and movable with respect to the ankle frame 112. The toe frame 132 can be positioned at a location corresponding to a toe or toes of a natural foot. The toe frame 132 can have at least one revolute joint to act as the toe or toes of a natural foot. In one aspect, the toe frame 132 can have a toe joint 136 and a second joint 140 positioned behind the toe joint 136. In one aspect, the toe frame 132 can be formed of metal, such as aluminum, and can be formed by machining or casting.

The series-elastic actuator 108 can comprise a linear actuator 144. The linear actuator 144 can be coupled to and between the ankle frame 112 and the foot member 128. In one aspect, the linear actuator 144 can be coupled to and between the first and second joints 124 and 140 of the ankle frame 112 and the toe frame 132. The linear actuator 144 can comprise a prismatic joint with a one-degree-of-freedom kinematic pair constraining the motion of two bodies to sliding along a common axis. The linear actuator 144 can move the foot member 128 with respect to the ankle frame 112. In one aspect, the linear actuator 144 can move and/or pivot the toe frame 132 with respect to the ankle frame 112.

The linear actuator 144 can have a drive motor 150. In one aspect, the drive motor 150 can be an electric motor with rotational output. The linear actuator 144 can also have a screw 154 coupled to the drive motor 150 and rotatable by the drive motor 150. The linear actuator 144 can also have a nut 158 that can be engaged by the screw 154. Rotation of the screw 154 can move the nut 158 along the screw 154. Thus, the drive motor 150 can be coupled to the screw 154 and can rotate the screw 154 relative to the nut 158. As the nut 158 moves along the screw 154, the foot member 128 and the toe frame 132 can be moved and/or pivoted with respect to the ankle frame 112. In one aspect, the screw 154 can be a ball screw and the nut 158 can be a ball nut. The ball nut 158 can retain a plurality of balls in helical grooves of the ball screw 154 and the ball nut 158. In another aspect, one end of the screw 154 can be retained in a bearing 162 coupled to the ankle frame 112.

In one aspect, the linear actuator 144 can also have a spring 166 coupled between the ankle frame 112 and the foot member 128 and the toe frame 132. The spring 166 can be coupled to the screw 154 and the nut 158. In one aspect, the nut 158 can be coupled to the spring 166. Thus, the screw 154 can extend between the first joint 124 of the ankle frame 112 and the nut 158, while the spring 166 can extend between the nut 158 and the second joint 140 of the toe frame 132. The spring 166 and the screw 154 can be coupled in series and inline. Thus, the prismatic joint or linear actuator 144 and the spring 166 can be coupled in series. In one aspect, the linear actuator 144 and the spring 166 can form an integrated series-elastic actuator 108 with the screw 154 in series with the spring 166 and extending between the first and second joints 124 and 140.

In one aspect, a spring mount 170 can be attached to an end of the spring 166. The spring mount 170 can have a helical groove with a pitch substantially matching a pitch of the spring 166 and receiving a portion of the spring. The nut 158 can be coupled to the spring mount 170. A bore can extend through the spring mount 170 and can receive the screw 154 therethrough as the screw 154 advances and retracts from the nut 158 during rotation. The screw 154 can extend at least partially into the spring 166 with the spring 166 circumscribing at least a portion of the screw 154. The spring 166 and the helical groove of the spring mount 170 can have an interference fit. A first interference fit can be between an inner diameter of the spring 166 and a minor diameter of the helical groove. A second interference fit can be between a coil height of the spring 166 and a thread height of the helical groove. A pair of spring mounts 170 and 174 can each capture a different end of the spring 166. An aft spring mount 170 can couple an aft end of the spring 166 to the screw 154 and a fore spring mount 174 can couple a fore end of the spring 166 to the toe frame 132. The spring 166 can have a different length of active coils in extension and compression. Thus, the spring 166 can have a different stiffness in tension and compression.

Figure 7:
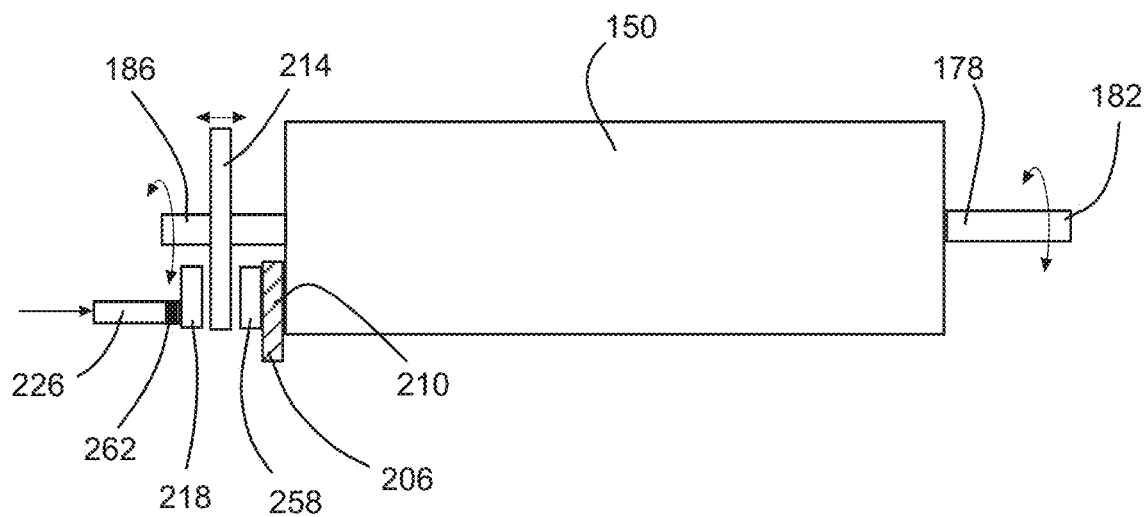

Referring to FIG. 7, the drive motor 150 can have a drive shaft 178 with opposite first and second ends 182 and 186 extending from the drive motor 150. Referring again to FIG. 1c, the first end 182 of the drive shaft 178 can be coupled to the screw 154. In one aspect, a gearbox 190 can be coupled to the first end 182 of the drive shaft 178, and between the first end 182 of the drive shaft 178 of the drive motor 150 and the screw 154. In another aspect, the gearbox 190 can be a non-back-drivable gear box. The gearbox 190 can have a gear reduction ratio to resist a force applied to the foot member from backdriving the linear actuator 144.

Referring again to FIGS. 1a and 1b, the locking mechanism 104 can selectively engage the drive motor 150 to selectively lock movement of the drive motor 150. Thus, the locking mechanism 104 can also resist a force on the foot member 128 from backdriving the linear actuator 144. In one aspect, the locking mechanism 104 can engage and be coupled to the second end 186 of the drive shaft 178.

The prosthesis 100 can have at least two modes of operation, including: an active mode and a passive mode. In the active mode, the drive motor 150 can be powered, and the locking mechanism 104 can be unlocked. The active mode can be associated with lower torque ambulation activities. In the passive mode, the drive motor 150 can be unpowered, and the locking mechanism 104 can be locked. The passive mode can be associated with higher torque ambulation activities.

In one aspect, the locking mechanism 104 can engage the drive motor 150 under speed and torque. The locking mechanism 104 can engage the drive motor 150 under load with the foot and ankle prosthesis 100 transitioning between active and passive modes, and without waiting for the locking mechanism 104 to lock in order to apply a damping torque. Thus, the locking mechanism 104 can be a brake mechanism and controlled damper. In another aspect, the locking mechanism 104 can engage the drive motor 150 in both directions of the linear actuator 144. Thus, the locking mechanism 104 can engage in both dorsiflexion and plantarflexion of the prosthesis 100. In another aspect, the locking mechanism 104 can remain in either a locked or unlocked position without power, as discussed herein. In another aspect, the locking mechanism 104 can apply a variable range of torque to the drive shaft 178 of the drive motor 150.

Figure 2A:
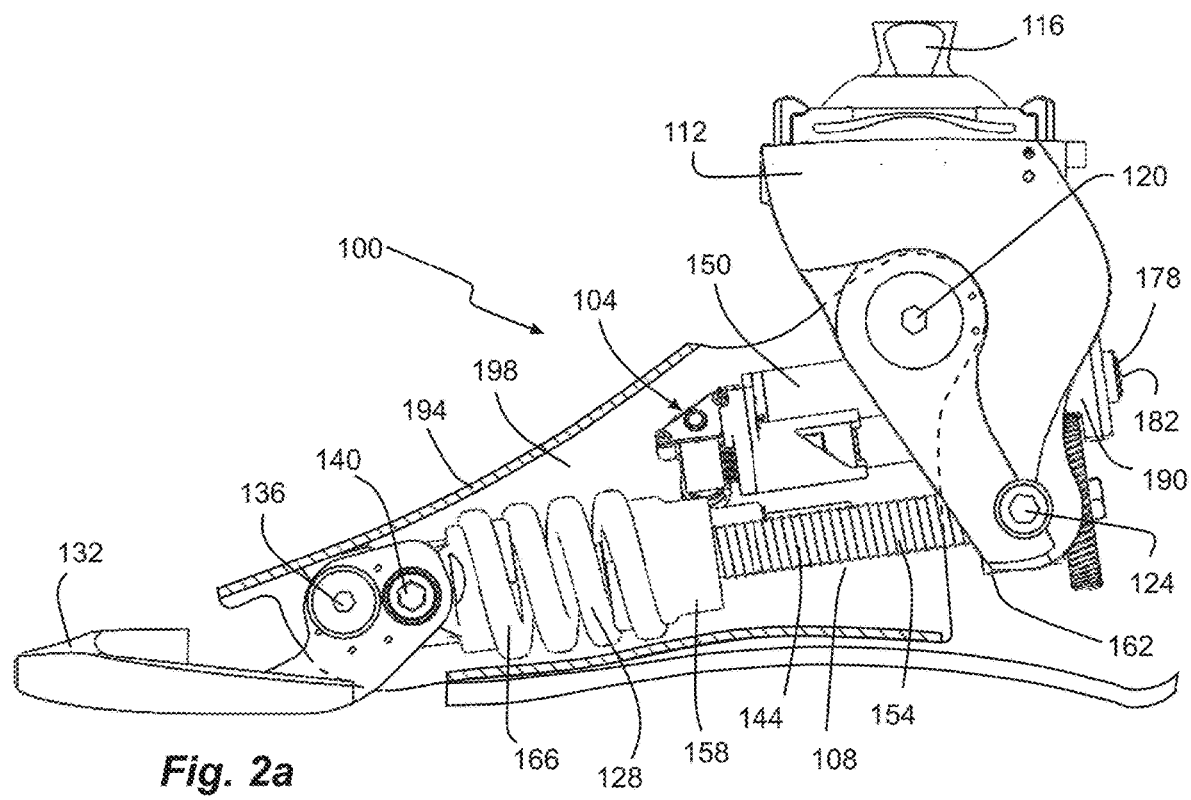
FIG. 2a is a partial cross-sectional side view of the foot and ankle prosthesis of FIG. 1a, shown with the foot shell in cross-section for visibility.
Figure 2B:
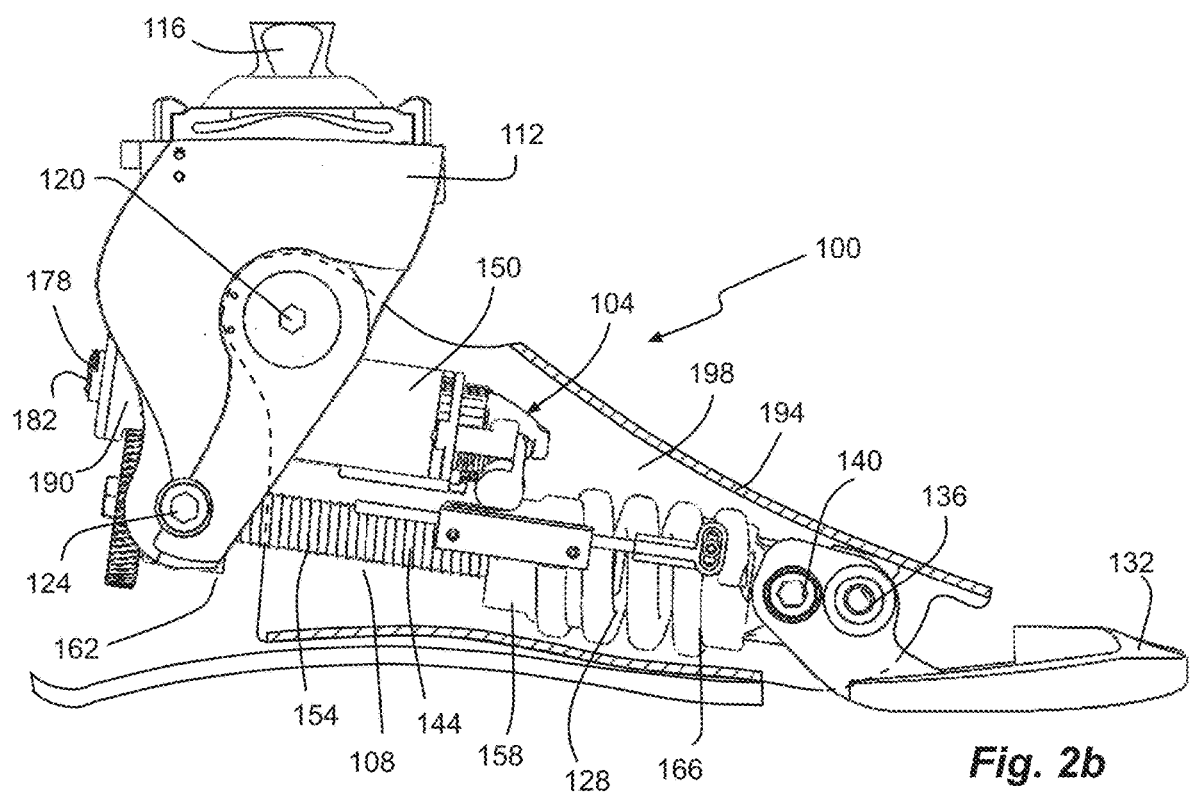

FIGS. 2a and 2b illustrate the foot and ankle prosthesis 100 with a foot shell 194 in cross-section. The foot shell 194 can be pivotally coupled to and between the ankle joint 120 of the ankle frame 112 and the toe joint 136 of the toe frame 132. Thus, the foot shell 194 can pivot with respect to the ankle frame 112, and the toe frame 132 can pivot with respect to the foot shell 194 and the ankle frame 112. The foot shell 194 can have a hollow 198 therein. In one aspect, the linear actuator 144 and the locking mechanism 104 can be at least partially located in the hollow 198 of the foot shell 194. In another aspect, the drive motor 150 can be at least partially located in the hollow 198 of the foot shell 194. The drive motor 150 can be located above the screw 154 and parallel with the screw 154. An end of the drive motor 150 with the first end 182 of the drive shaft 178, and the gearbox 190, can extend out of the hollow 198 of the foot shell 194 and into the ankle frame 112. Similarly, an end of the screw 154, the bearing 162 and associated gears can extend out of the hollow 198 of the foot shell 194 and into the ankle frame 112. Locating a portion of the linear actuator 144 in the foot shell 194, including a portion of the drive motor 150, can save space, such as for amputees with a longer residual limb. In addition, locating a portion of the linear actuator 144 in the foot shell 194, including a portion of the drive motor 150, can minimize the rear dimension of the ankle and enable the ankle and prosthesis 100 to fit into a foot shell and/or unmodified shoe, represented at 200 in FIG. 3.

In one aspect, the foot shell 194 can extend around an arch portion of the prosthesis 100 corresponding to an arch portion of a natural foot with open ends at the toe and heel. In another aspect, the foot shell 194 can be formed of a composite material, such as resin impregnated carbon fiber.

Figure 3:
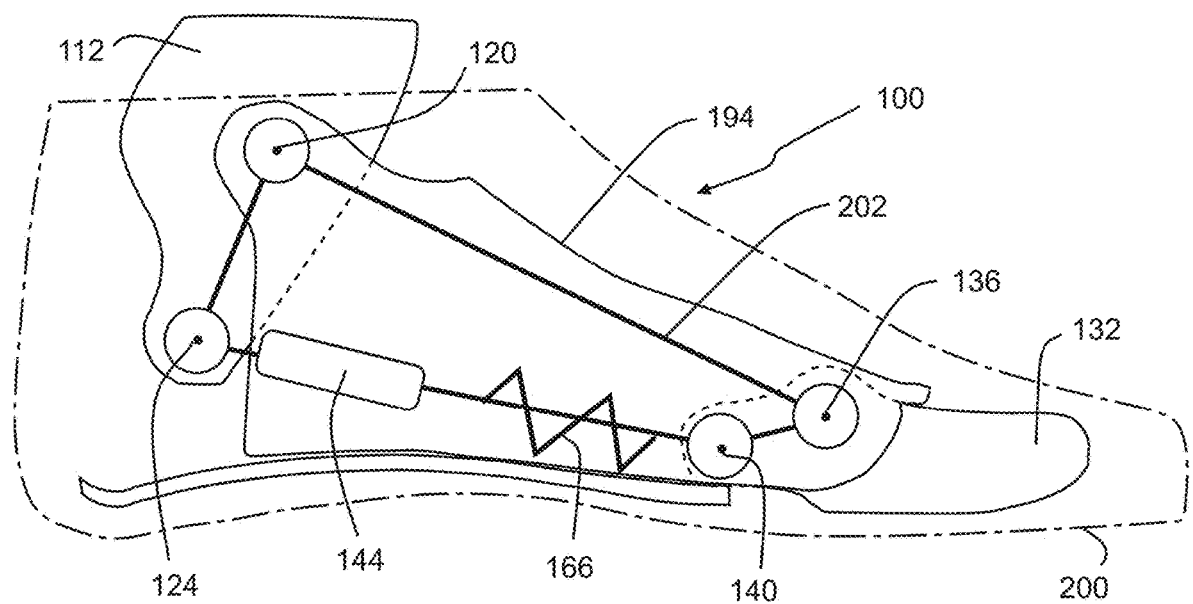

FIG. 3 illustrates a schematic of the foot and ankle prosthesis 100. In one aspect, the foot shell 194 can form a rigid link between the ankle joint 120 and the toe joint 136. In another aspect, the ankle frame 112, the toe frame 132, the foot shell 194 and the prismatic joint, or linear actuator 144, with the spring 166 can form a four-bar linkage 202.

Figure 4:
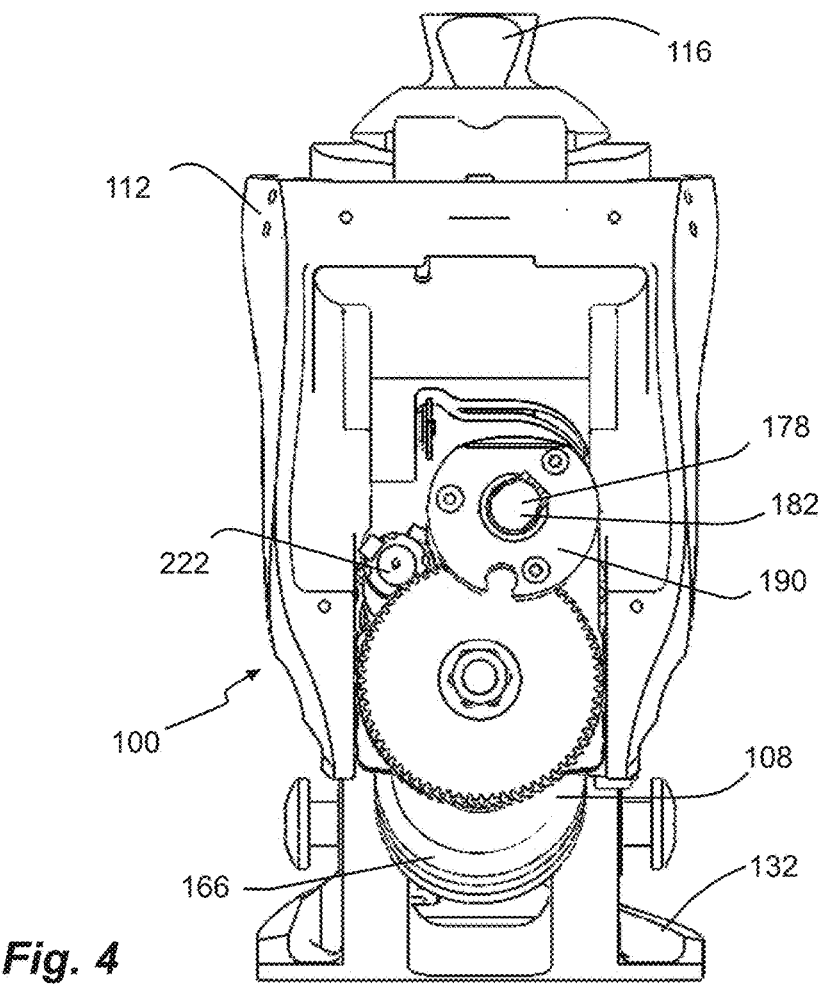

FIG. 4 illustrates a rear view of the foot and ankle prosthesis 100. A portion of the drive motor 150 with the first end 182 of the drive shaft 178 and the gearbox 190 can extend into the ankle frame 112. In addition, the drive motor 150 can be located above the screw 154.

FIGS. 5a-d illustrate the locking mechanism 104 of the foot and ankle prosthesis 100. The locking mechanism 104 can have a lock housing 206 enclosing at least a portion of the locking mechanism 104. In one aspect, the lock housing 206 can be mounted to the linear actuator 144, such as to the drive motor 150. In another aspect, the lock housing 206 can have a mounting plate 210 mounted to the drive motor 150.

The locking mechanism 104 can utilize a rotor 214 and at least one brake pad 218. The brake pad(s) 218 can be driven or actuated by a brake motor 222 and a cam 226. The rotor 214 can be coupled to the second end 186 of the drive shaft 178 of the drive motor 150, opposite the first end 182 of the drive shaft 178 coupled to the gearbox 190 and the screw 154. The brake pad 218 can be positioned proximate the rotor 214 to selectively abut to the rotor 214. The rotor 214 can be keyed and fixed radially to the drive shaft 178 with the rotor 214 and the drive shaft 178 rotating together. In one aspect, the rotor 214 can have an aperture 230 shaped as a prism, such as a hexagon, to rotationally fix the rotor 214 to the drive shaft 178 while allowing the rotor 214 to slide axially along the drive shaft 178. The second end 186 of the drive shaft 178, or an adaptor thereon, can similarly be shaped as the aperture 230. The rotor 214 can slide axially along the drive shaft 178 to self-center the rotor 214 between the brake pads 218, as discussed further herein.

The locking mechanism 104 can have a brake motor 222. In one aspect, the brake motor 222 can be an electric motor with rotational motion. In another aspect, the brake motor 222 can be positioned proximate the drive motor 150. The brake motor 222 can be mounted to the drive motor 150 with the lock housing 206 and the mounting plate 210. In another aspect, the brake motor 222 can include a gearbox and/or a planetary gear system 234. In another aspect, the brake motor 222 can engage a worm drive 236 with a worm or worm screw 240 meshing with a worm gear or worm wheel 244. The use of a worm drive 236 can change the rotational axis of motion from parallel with the brake motor 222 to transverse to the brake motor 222.

The worm drive 236 can be coupled to the cam 226. The cam 226 can be carried by an axle 248 driven by the worm gear 240 or worm wheel 244. The axle 248 can be rotationally mounted to the lock housing 206 with rotational bearings on opposite ends of the axle 248. The cam 226 can engage the brake pads 218, such as a first movable brake pad 218. In one aspect, the cam 226 can engage the brake pad 218 directly. In another aspect, the cam 226 can drive a piston that can drive the brake pad 218.

Figure 6A:
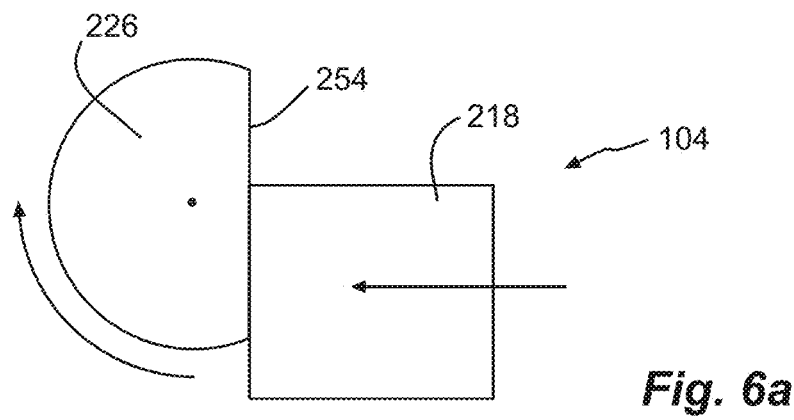
FIG. 6a is a partial schematic illustration of the locking mechanism of FIG. 5a, shown in an unlocked position.
Figure 6B:
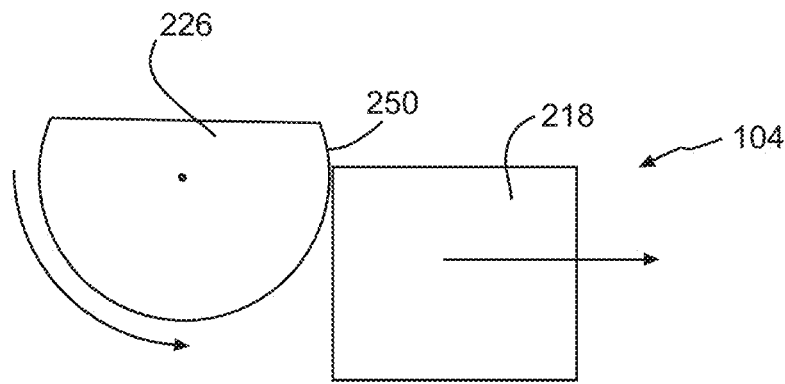
FIG. 6b is a partial schematic illustration of the locking mechanism of FIG. 5a, shown in a locked position.

FIGS. 6a and 6b illustrate the function of the cam 226 and the brake pad(s) 218 of the locking mechanism 104. The cam 226 can engage the first movable brake pad 218. The cam 226 can have a lobe or extension 250 with a greater radial length to press the brake pad 218 towards the rotor 214, as shown in FIG. 6b. In addition, the cam 226 can have a heel 254 away from the extension 250 with a lesser radial length to release the brake pad 218 from the rotor 214, as shown in FIG. 6a. As discussed herein, the cam 226 can directly engage the brake pad 218. In another aspect, the cam 226 can engage a piston between the cam 226 and the brake pad 218. The brake motor 222 can be coupled to the cam 226 as described herein to selectively turn the cam 226. A rotational axis of the cam 226 can be aligned with a linear axis of brake pad 218 or piston so that axial force of the brake pad 218 is against the rotational axis of the cam 226, essentially locking relative movement between the cam 226 and the brake pad 218. The cam 226, and thus the locking mechanism 104, can remain in either a locked or unlocked position without power.

Figure 5A:
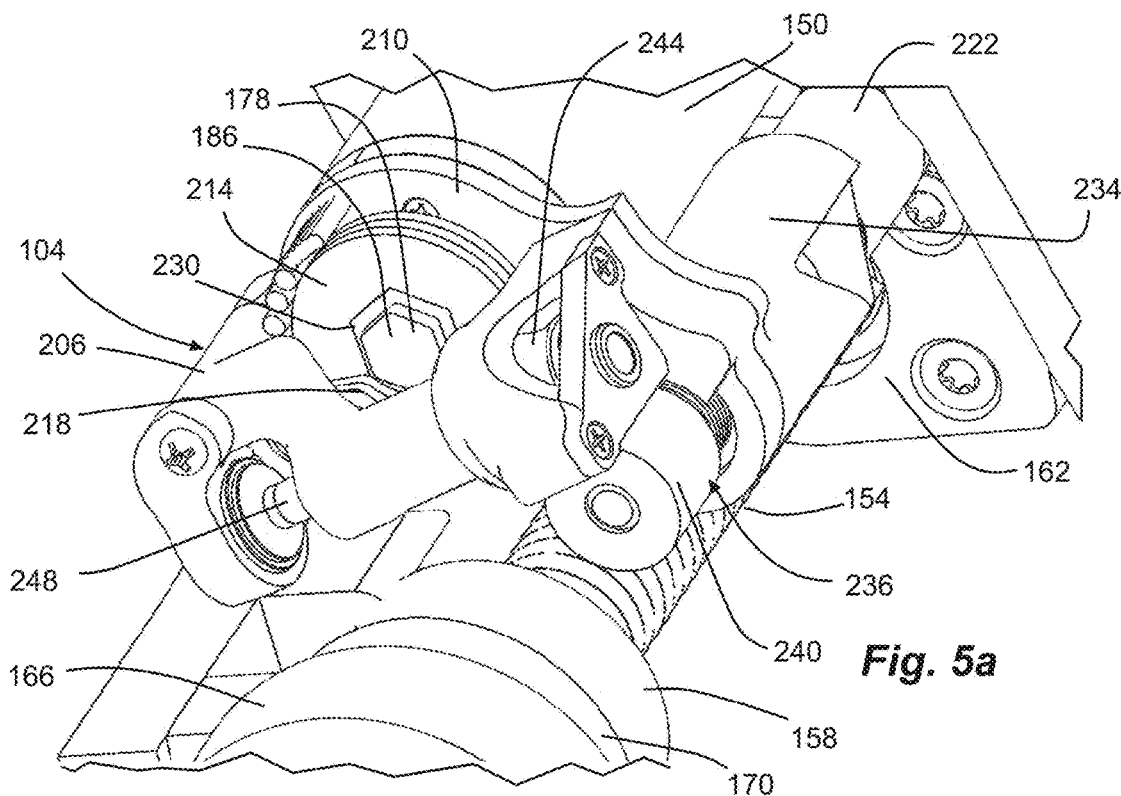
FIG. 5a is a partial detailed perspective view of a locking mechanism of the foot and ankle prosthesis of FIG. 1a in accordance with one example, and shown with the foot shell removed for visibility.
Figure 5B:
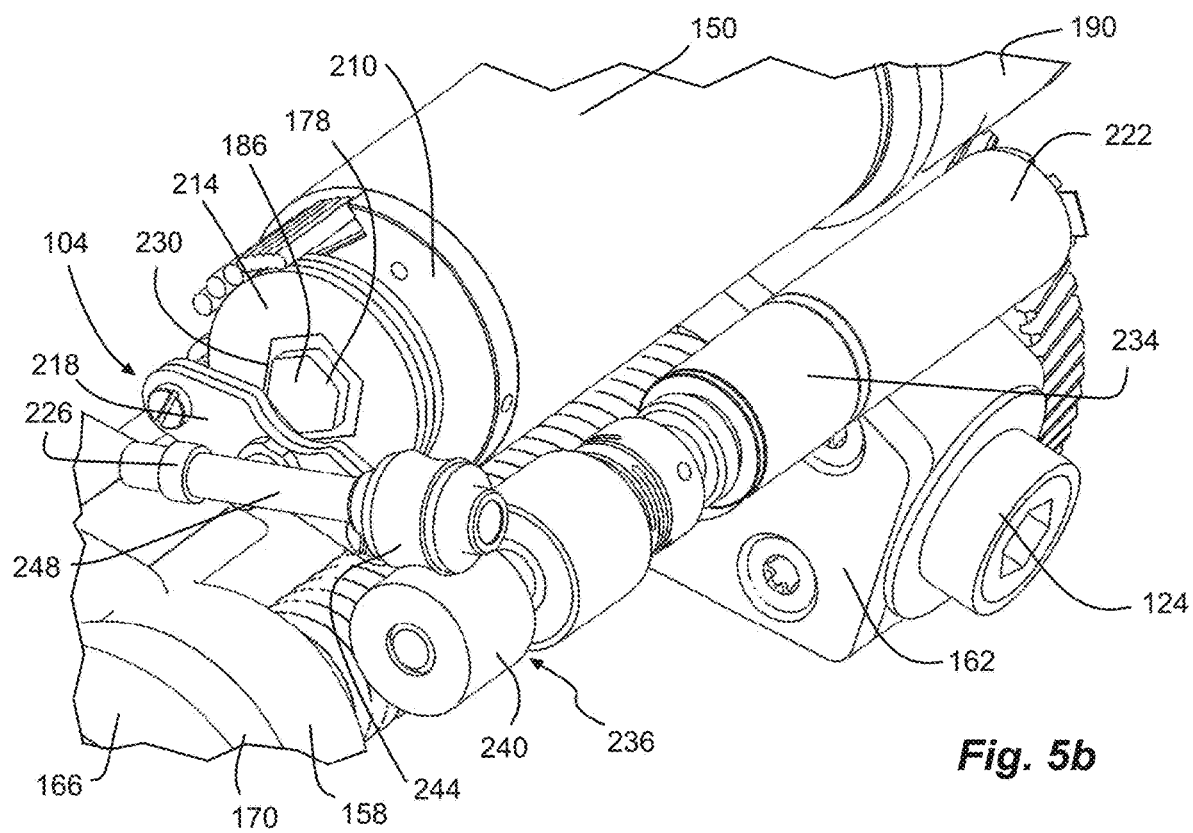
FIG. 5b a partial detailed perspective view of the locking mechanism of the foot and ankle prosthesis of FIG. 1a, shown with a lock housing removed for visibility.
Figure 5C:
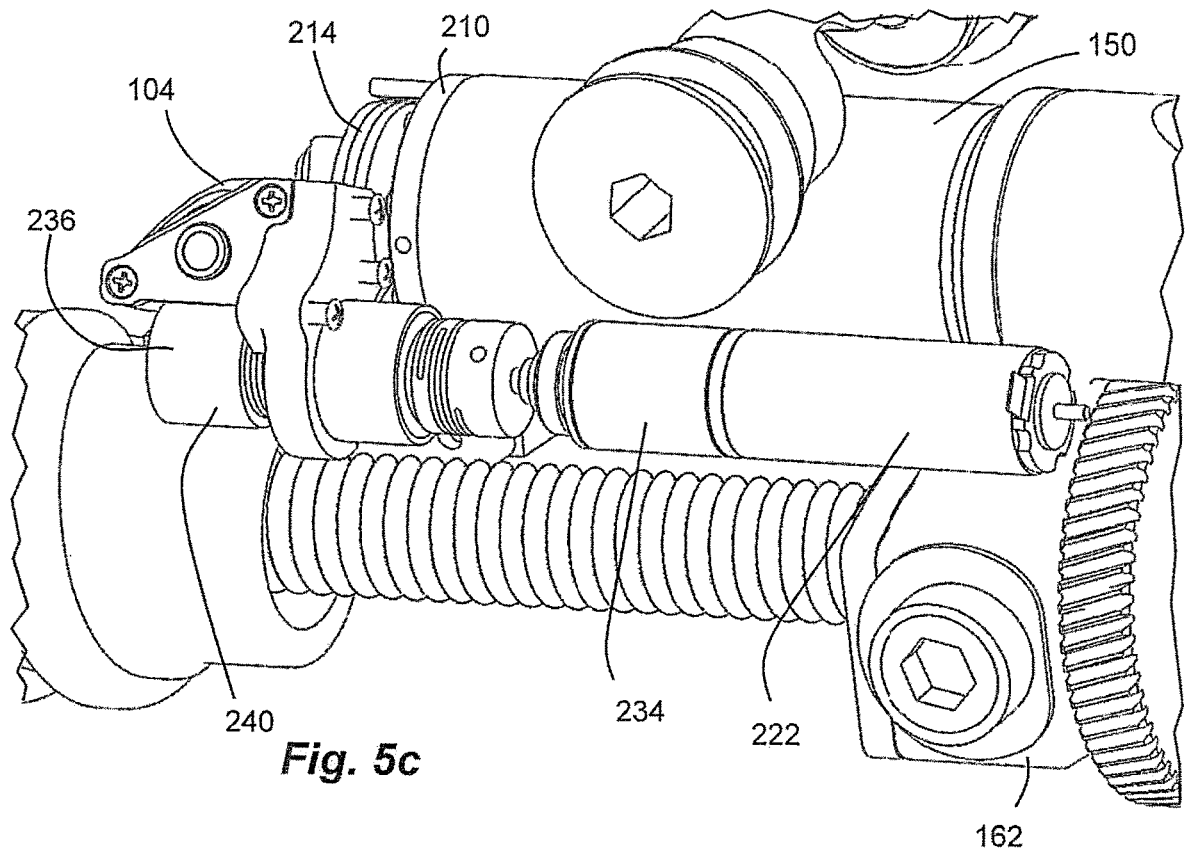
Figure 5D:
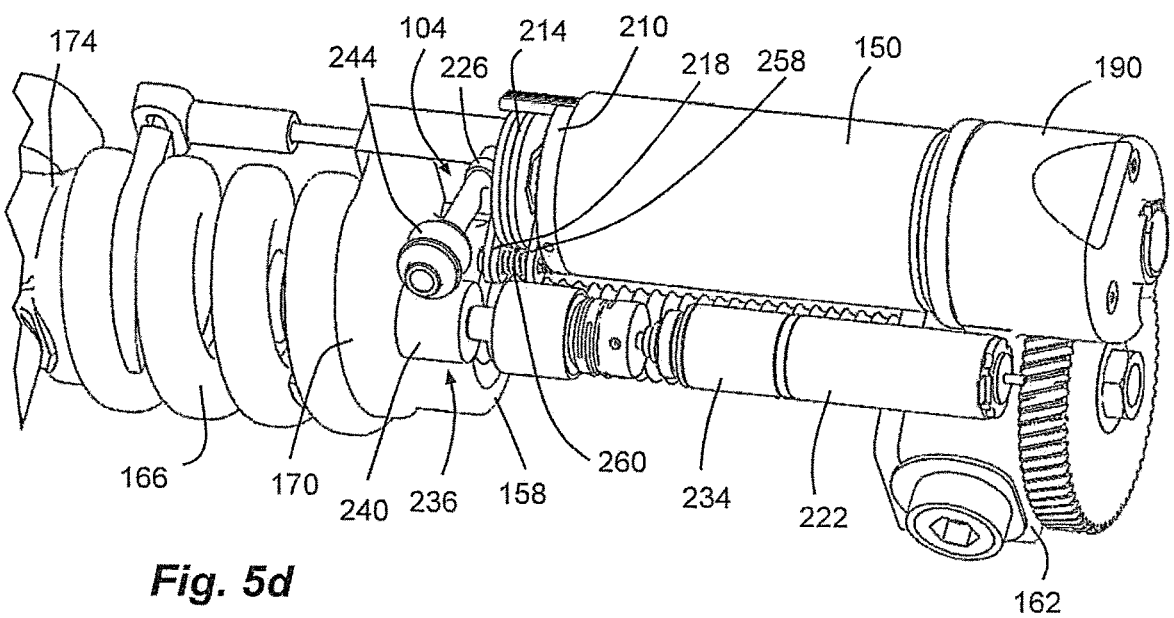
FIG. 5d is a partial detailed perspective view of the locking mechanism of the foot and ankle prosthesis of FIG. 1a, shown with the lock housing removed for visibility.

FIG. 7 further illustrates the function of the locking mechanism 104. In one aspect, a pair of brake pads 218 and 258 can selectively abut to both sides of the rotor 214, and can selectively pinch the rotor 214 between the pair of brake pads 218 and 258. A first brake pad 218 can be a movable brake pad 218 and can be located on a first side of the rotor 214. A second brake pad 258 can be a stationary brake pad 258 and can be located on a second side of the rotor 214. The second stationary brake pad 258 can be carried by the lock housing 206 and/or mounting plate 210 of the locking mechanism 104. The brake pads 218 and 258 can be carried on pins with springs 260 to bias the brake pads 218 and 258 away from one another and the rotor 214, as shown in FIG. 5d.

In another aspect, the rotor 214 can be slidably positioned on the second end 186 of the drive shaft 178. The rotor 214 can slide axially on the drive shaft 178 to self-center the rotor 214 between the pair of brake pads 218 and 258. The rotor 214 can be keyed and fixed radially to the drive shaft 178 with the rotor 214 and the drive shaft 178 rotating together. As described herein with respect to FIG. 5a, the rotor 214 can have an aperture 230 with a prism shape, such as a hexagon, to rotationally fix the rotor 214 to the drive shaft 178 while allowing the rotor 214 to slide axially along the drive shaft 178.

In one aspect, a resilient pad 262 can be positioned between the cam 226 and the first movable brake pad 218. In another aspect, the resilient pad 262 can be positioned between the cam 226 and the piston. The resilient pad 262 can prevent and resist any backlash in the locking mechanism 104 from disengaging the brake pads 218 and 258 and rotor 214 when the non-backdrivable worm drive 236 should be supporting the braking torque. In one aspect, the resilient pad 262 can be a 1 mm thick piece of 60A durometer rubber. The resilient pad 262 can provide compliance to the locking mechanism 104 in case the worm drive 236 backs off slightly due to backlash so that there will still be significant force applied to the brake pads 218 and 258 and the rotor 214.

Referring again to FIGS. 2a and 2b, the cam 226, the brake pad(s) 218 and 258, and the rotor 114 can be located in the hollow 198 of the foot shell 194. In another aspect, the brake motor 222 can be at least partially located in the hollow 198 of the foot shell 194. An end of the brake motor 222 can extend out of the hollow 198 and into the ankle frame 112.

Referring again to FIG. 4, the brake motor 222 and the drive motor 150 can be positioned side-by-side and proximate one another. The brake motor 222 can be located below the drive shaft 178 of the drive motor 150 and above an axis of the screw 154. Thus, the prosthesis 100 can have a low height for amputees with longer residual limbs.

Figure 8A:
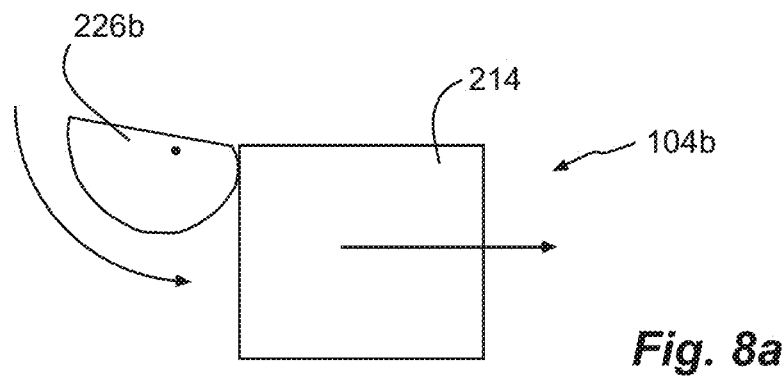
FIG. 8a is a partial schematic illustration of a locking mechanism of the foot and ankle prosthesis of FIG. 1a in accordance with one example, shown in an unlocked position.
Figure 8B:
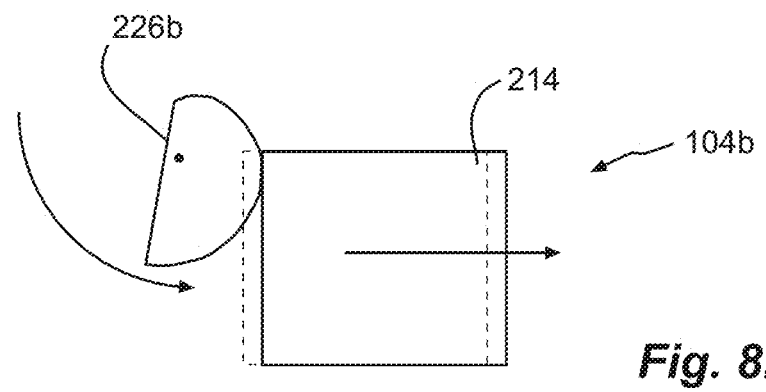
FIG. 8b is a partial schematic illustration of the locking mechanism of the foot and ankle prosthesis of FIG. 8a, shown in a torque damping position.
Figure 8C:
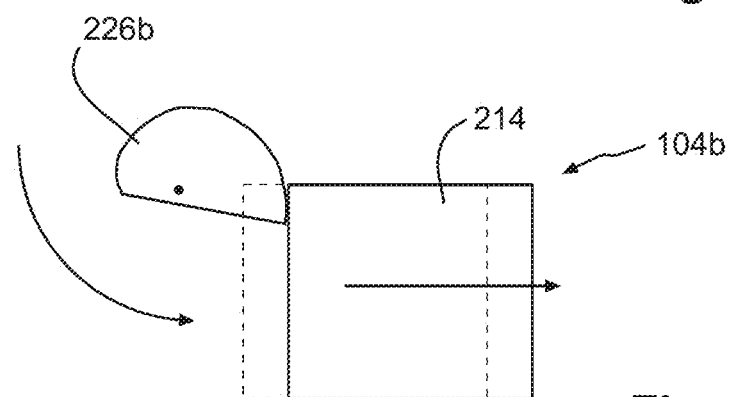
FIG. 8c is a partial schematic illustration of the locking mechanism of the foot and ankle prosthesis of FIG. 8a, shown in a locked position.

FIGS. 8*a-c* illustrate a torque damping function of the locking mechanism 104*b*. In one aspect, the cam 226*b* can have multiple positions with respect to the brake pad 218, and thus the rotor 214, to apply a damping torque to the drive motor 150. In one aspect, the cam 226*b* can have a continuously variable length from a pivot axis, such as a helical shape. In another aspect, the cam 226 described herein can have a fixed length with multiple radial positions to achieve an effective variable distance from the pivot axis. The locking mechanism 104 or 104*b* can act without completely locking the drive motor 105 to apply a damping torque. Thus, the locking mechanism 104 or 104*b* can be used as a controlled damper and/or a braking mechanism.

The motors 222 and 150 can be powered by a power source, such as a battery pack, carried by a housing mountable to the pylon.

The motors 222 and 150 can be controlled by one or more controllers associated with the prosthesis 100.

Sensors can be carried by the prosthesis 100 and utilized by the controller(s). For example, a linear potentiometer can be positioned proximate the spring 166 to measure deflection of the spring 166.

Additional Examples

The following is a non-exhaustive list of example embodiments provided as numbered items.

1. A semi-powered foot and ankle prosthesis, comprising: an ankle frame configured to be coupled to a connector; a foot member coupled to the ankle frame and movable with respect to the ankle frame; a linear actuator coupled to and between the ankle frame and the foot member, and configured to move the foot member with respect to the ankle frame, and the linear actuator having a drive motor; and a locking mechanism selectively engaging the drive motor and configured to selectively lock movement of the drive motor to resist a force on the foot member from backdriving the linear actuator.

2. The foot and ankle prosthesis of item 1, further comprising: the ankle frame having a first joint; the foot member comprising a toe frame spaced-apart from and movable with respect to the ankle frame, and the toe frame having a second joint; and the linear actuator coupled to and between the first and second joints.

3. The foot and ankle prosthesis of item 2, further comprising: a foot shell pivotally coupled to and between an ankle joint of the ankle frame and a toe joint of the toe frame; the foot shell forming a rigid link between the ankle joint and the toe joint; the foot shell having a hollow therein; and the linear actuator and the locking mechanism being at least partially located in the hollow of the foot shell.

4. The foot and ankle prosthesis of item 2, further comprising: a foot shell pivotally coupled to and between an ankle joint of the ankle frame and a toe joint of the toe frame; the foot shell forming a rigid link between the ankle joint and the toe joint; the foot shell having a hollow therein; and the drive motor being at least partially located in the hollow of the foot shell.

5. The foot and ankle prosthesis of item 1, further comprising: at least two modes of operation, including: an active mode in which the drive motor is powered, and the locking mechanism is unlocked, and associated with lower torque ambulation activities; and a passive mode in which the drive motor is unpowered, and the locking mechanism is locked, and associated with higher torque ambulation activities.

6. The foot and ankle prosthesis of item 1, further comprising: a drive shaft having first and second ends extending from the drive motor; a gearbox coupled to the first end of the drive shaft; and the locking mechanism engaging the second end of the drive shaft.

7. The foot and ankle prosthesis of item 1, wherein the linear actuator comprises an integrated series elastic actuator, comprising: a screw coupled to the drive motor to rotate the screw; a nut engaged by the screw and with rotation of the screw moving the nut along the screw; and a spring coupled to the nut with the screw and spring coupled in series.

8. The foot and ankle prosthesis of item 7, further comprising: the drive motor having a drive shaft with opposite first and second ends; the first end of the drive shaft being coupled to the screw; and the second end of the drive shaft being coupled to the locking mechanism.

9. The foot and ankle prosthesis of item 8, further comprising: a non-back-drivable gear box coupled between the first end of the drive shaft and the screw, the gear box having a gear reduction ratio configured to resist a force applied to the foot member from backdriving the linear actuator.

10. The foot and ankle prosthesis of item 1, wherein the locking mechanism further comprises: a rotor coupled to a drive shaft of the motor; and at least one brake pad positioned proximate the rotor and selectively abutting the rotor.

11. The foot and ankle prosthesis of item 10, wherein the locking mechanism further comprises: a brake motor; and a non-back-drivable gear box coupled between the brake motor and the at least one brake pad, the gear box having a worm driven by the brake motor and a worm wheel engaging the worm.

12. The foot and ankle prosthesis of item 10, wherein the locking mechanism further comprises: the at least one brake pad including a pair of brake pads, including: a first movable brake pad on a first side of the rotor; and a second stationary brake pad on a second side of the rotor and carried by a frame of the locking mechanism.

13. The foot and ankle prosthesis of item 10, wherein the locking mechanism further comprises: the rotor being slidably positioned on the drive shaft; and the rotor being keyed radially to the drive shaft with the rotor and the drive shaft rotating together.

14. The foot and ankle prosthesis of item 10, wherein the locking mechanism further comprises: a cam engaging the at least one brake pad and having a lobe with a greater radial length configured to press the brake pad towards the rotor, and a heel with a lesser radial length configured to release the brake pad from the rotor; and a brake motor coupled to and selectively turning the cam.

15. The foot and ankle prosthesis of item 14, wherein the cam has multiple positions with respect to the at least one brake pad and the rotor configured to apply a damping torque to the drive motor.

16. The foot and ankle prosthesis of item 14, wherein the locking mechanism further comprises: a resilient pad positioned between the cam and the at least one brake pad.

17. The foot and ankle prosthesis of item 14, wherein the locking mechanism further comprises: the brake motor and the drive motor positioned side-by-side and proximate one another.

18. The foot and ankle prosthesis of item 14, further comprising: the ankle frame having an ankle joint; the foot member comprising a toe frame spaced-apart from and movable with respect to the ankle frame, and the toe frame having a toe joint; a foot shell pivotally coupled to and between the ankle joint of the ankle frame and the toe joint of the toe frame; the foot shell having a hollow therein; the drive motor and the brake motor being at least partially located in the hollow of the foot shell; and the cam and the at least one brake pad being located in the hollow of the foot shell.

19. The foot and ankle prosthesis of item 1, wherein the locking mechanism engages the drive motor under speed and torque; and wherein the locking mechanism engages the drive motor under load with the prosthetic foot and ankle transitioning between active and passive modes without waiting for the locking mechanism to lock.

20. The foot and ankle prosthesis of item 1, wherein the locking mechanism engages the drive motor in both directions of the linear actuator, and in dorsiflexion and plantarflexion of the prosthetic foot and ankle.

21. The foot and ankle prosthesis of item 1, wherein the locking mechanism remains in either a locked or unlocked position without power.

22. The foot and ankle prosthesis of item 1, wherein the locking mechanism applies a variable range of torque to a drive shaft of the drive motor.

23. A semi-powered foot and ankle prosthesis, comprising: an ankle frame configured to be coupled to a connector; a foot member coupled to the ankle frame and movable with respect to the frame; a linear actuator coupled to and between the ankle frame and the foot member, and configured to move the foot member with respect to the ankle frame, and the linear actuator having a drive motor; and a locking mechanism selectively engaging the drive motor and configured to selectively lock movement of the drive motor to resist a force on the foot member from backdriving the linear actuator, the locking mechanism comprising: a rotor coupled to a drive shaft of the motor; at least one brake pad positioned proximate the rotor and selectively abutting the rotor; a cam engaging the at least one brake pad and having a lobe with a greater radial length configured to press the brake pad towards the rotor, and a heel with a lesser radial length configured to release the brake pad from the rotor; and a brake motor coupled to and selectively turning the cam.

24. A semi-powered foot and ankle prosthesis, comprising: an ankle frame configured to be coupled to a connector; a foot shell pivotally coupled to the ankle frame; a toe frame pivotally coupled to the foot shell opposite the ankle frame; a spring coupled between the ankle frame and the toe frame; a prismatic joint coupled between the ankle frame and the toe frame; the prismatic joint and the spring being coupled in series; the prismatic joint comprising a nut coupled to the spring and a screw extending between the ankle frame and the nut; a motor coupled to the screw and configured to rotate the screw relative to the nut; a locking mechanism coupled to the drive motor and configured to selectively lock movement of the drive motor to resist a force on the foot member from backdriving the linear actuator, the locking mechanism comprising: a rotor rotationally coupled to the screw and an output of the motor; a brake pad proximate the rotor and selectively engagable with the rotor to resist rotation of the rotor and thus the screw; a cam engaging the piston and having a lobe with a greater radial length configured to press the brake pad towards the rotor, and a heel with a lesser radial length configured to release the brake pad from the rotor; and a brake motor coupled to and selectively turning the cam.

While the flowcharts presented for this technology may imply a specific order of execution, the order of execution may differ from what is illustrated. For example, the order of two or more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions and may even be distributed over several different code segments, among different programs and across several memory devices. Similarly, operational data may be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described here may also be stored on a computer readable storage medium that includes volatile and non-volatile, removable and non-removable media implemented with any technology for the storage of information such as computer readable instructions, data structures, program modules, or other data. Computer readable storage media include, but is not limited to, a non-transitory machine readable storage medium, such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

What is claimed is:

1. A semi-powered foot and ankle prosthesis, comprising:
    an ankle frame configured to be coupled to a connector and the ankle frame having a first joint;
    a foot member coupled to the ankle frame and movable with respect to the ankle frame, the foot member comprising a toe frame spaced-apart from and movable with respect to the ankle frame, and the toe frame having a second joint;
    a linear actuator coupled to and between the ankle frame and the foot member, and coupled to and between the first and second joints, and configured to move the foot member with respect to the ankle frame, and the linear actuator having a drive motor;
    a locking mechanism selectively engaging the drive motor and configured to selectively lock movement of the drive motor to resist a force on the foot member from backdriving the linear actuator;
    a foot shell pivotally coupled to and between an ankle joint of the ankle frame and a toe joint of the toe frame, the foot shell forming a rigid link between the ankle joint and the toe joint, the foot shell having a hollow therein; and
    at least one of:
        the linear actuator and the locking mechanism being at least partially located in the hollow of the foot shell; and
        the drive motor being at least partially located in the hollow of the foot shell.

2. The foot and ankle prosthesis of claim 1, further comprising:
    at least two modes of operation, including:
        an active mode in which the drive motor is powered, and the locking mechanism is unlocked, and associated with lower torque ambulation activities; and
        a passive mode in which the drive motor is unpowered, and the locking mechanism is locked, and associated with higher torque ambulation activities.

3. The foot and ankle prosthesis of claim 1, further comprising:
    a drive shaft having first and second ends extending from the drive motor;
    a gearbox coupled to the first end of the drive shaft; and
    the locking mechanism engaging the second end of the drive shaft.

4. The foot and ankle prosthesis of claim 1, wherein the linear actuator comprises an integrated series elastic actuator, comprising:
    a screw coupled to the drive motor to rotate the screw;
    a nut engaged by the screw and with rotation of the screw moving the nut along the screw; and
    a spring coupled to the nut with the screw and spring coupled in series.

5. The foot and ankle prosthesis of claim 4, further comprising:
    the drive motor having a drive shaft with opposite first and second ends;
    the first end of the drive shaft being coupled to the screw; and
    the second end of the drive shaft being coupled to the locking mechanism.

6. The foot and ankle prosthesis of claim 5, further comprising:
    a non-back-drivable gear box coupled between the first end of the drive shaft and the screw, the gear box having a gear reduction ratio configured to resist a force applied to the foot member from backdriving the linear actuator.

7. The foot and ankle prosthesis of claim 1, wherein the locking mechanism further comprises:
    a rotor coupled to a drive shaft of the motor; and
    at least one brake pad positioned proximate the rotor and selectively abutting the rotor.

8. The foot and ankle prosthesis of claim 7, wherein the locking mechanism further comprises:
    a brake motor; and
    a non-back-drivable gear box coupled between the brake motor and the at least one brake pad, the gear box having a worm driven by the brake motor and a worm wheel engaging the worm.

9. The foot and ankle prosthesis of claim 7, wherein the locking mechanism further comprises:
    the at least one brake pad including a pair of brake pads, including:
    a first movable brake pad on a first side of the rotor; and
    a second stationary brake pad on a second side of the rotor and carried by a frame of the locking mechanism.

10. The foot and ankle prosthesis of claim 7, wherein the locking mechanism further comprises:
    the rotor being slidably positioned on the drive shaft; and
    the rotor being keyed radially to the drive shaft with the rotor and the drive shaft rotating together.

11. The foot and ankle prosthesis of claim 7, wherein the locking mechanism further comprises:
    a cam engaging the at least one brake pad and having a lobe with a greater radial length configured to press the brake pad towards the rotor, and a heel with a lesser radial length configured to release the brake pad from the rotor; and a brake motor coupled to and selectively turning the cam.

12. The foot and ankle prosthesis of claim 11, wherein the cam has multiple positions with respect to the at least one brake pad and the rotor configured to apply a damping torque to the drive motor.

13. The foot and ankle prosthesis of claim 11, wherein the locking mechanism further comprises:
a resilient pad positioned between the cam and the at least one brake pad.

14. The foot and ankle prosthesis of claim 11, wherein the locking mechanism further comprises:
the brake motor and the drive motor positioned side-by-side and proximate one another.

15. The foot and ankle prosthesis of claim 11, further comprising:
the ankle frame having an ankle joint;
the drive motor and the brake motor being at least partially located in the hollow of the foot shell; and
the cam and the at least one brake pad being located in the hollow of the foot shell.

16. The foot and ankle prosthesis of claim 1, wherein the locking mechanism engages the drive motor under speed and torque; and wherein the locking mechanism engages the drive motor under load with the foot and ankle prosthesis transitioning between active and passive modes without waiting for the locking mechanism to lock.

17. The foot and ankle prosthesis of claim 1, wherein the locking mechanism engages the drive motor in both directions of the linear actuator, and in dorsiflexion and plantarflexion of the foot and ankle prosthesis.

18. The foot and ankle prosthesis of claim 1, wherein the locking mechanism remains in either a locked or unlocked position without power.

19. The foot and ankle prosthesis of claim 1, wherein the locking mechanism applies a variable range of torque to a drive shaft of the drive motor.

20. The foot and ankle prosthesis of claim 1, wherein:
the locking mechanism engages the drive motor in both directions of the linear actuator, and in dorsiflexion and plantarflexion of the foot and ankle prosthesis;
the locking mechanism remains in either a locked or unlocked position without power; and
the locking mechanism applies a variable range of torque to a drive shaft of the drive motor.

21. A semi-powered foot and ankle prosthesis, comprising:
an ankle frame configured to be coupled to a connector;
a foot member coupled to the ankle frame and movable with respect to the frame;
a linear actuator coupled to and between the ankle frame and the foot member, and configured to move the foot member with respect to the ankle frame, and the linear actuator having a drive motor; and
a locking mechanism selectively engaging the drive motor and configured to selectively lock movement of the drive motor to resist a force on the foot member from backdriving the linear actuator, the locking mechanism comprising:
a rotor coupled to a drive shaft of the motor;
at least one brake pad positioned proximate the rotor and selectively abutting the rotor;
a cam engaging the at least one brake pad and having a lobe with a greater radial length configured to press the brake pad towards the rotor, and a heel with a lesser radial length configured to release the brake pad from the rotor; and
a brake motor coupled to and selectively turning the cam.

22. A semi-powered foot and ankle prosthesis, comprising:
an ankle frame configured to be coupled to a connector;
a foot shell pivotally coupled to the ankle frame;
a toe frame pivotally coupled to the foot shell opposite the ankle frame;
a spring coupled between the ankle frame and the toe frame;
a prismatic joint coupled between the ankle frame and the toe frame;
the prismatic joint and the spring being coupled in series;
the prismatic joint comprising a nut coupled to the spring and a screw extending between the ankle frame and the nut;
a drive motor coupled to the screw and configured to rotate the screw relative to the nut;
a locking mechanism coupled to the drive motor and configured to selectively lock movement of the drive motor to resist a force on the foot and ankle prosthesis from backdriving the linear actuator, the locking mechanism comprising:
a rotor rotationally coupled to the screw and an output of the drive motor;
a brake pad proximate the rotor and selectively engagable with the rotor to resist rotation of the rotor and thus the screw;
a cam engaging a piston and having a lobe with a greater radial length configured to press the brake pad towards the rotor, and a heel with a lesser radial length configured to release the brake pad from the rotor; and
a brake motor coupled to and selectively turning the cam.

23. A semi-powered foot and ankle prosthesis, comprising:
an ankle frame configured to be coupled to a connector;
a foot member coupled to the ankle frame and movable with respect to the ankle frame;
a linear actuator coupled to and between the ankle frame and the foot member, and configured to move the foot member with respect to the ankle frame, and the linear actuator having a drive motor; and
a locking mechanism selectively engaging the drive motor and configured to selectively lock movement of the drive motor to resist a force on the foot member from backdriving the linear actuator, wherein the locking mechanism further comprises:
a rotor coupled to a drive shaft of the motor; and
at least one brake pad positioned proximate the rotor and selectively abutting the rotor.

24. The foot and ankle prosthesis of claim 23, further comprising:
the ankle frame having a first joint;
the foot member comprising a toe frame spaced-apart from and movable with respect to the ankle frame, and the toe frame having a second joint;
the linear actuator coupled to and between the first and second joints;
a foot shell pivotally coupled to and between an ankle joint of the ankle frame and a toe joint of the toe frame;
the foot shell forming a rigid link between the ankle joint and the toe joint;
the foot shell having a hollow therein; and
at least one of:

the linear actuator and the locking mechanism being at least partially located in the hollow of the foot shell; and the drive motor being at least partially located in the hollow of the foot shell.

25. The foot and ankle prosthesis of claim 23, further comprising:

at least two modes of operation, including:

an active mode in which the drive motor is powered, and the locking mechanism is unlocked, and associated with lower torque ambulation activities; and a passive mode in which the drive motor is unpowered, and the locking mechanism is locked, and associated with higher torque ambulation activities.

26. The foot and ankle prosthesis of claim 23, wherein the locking mechanism further comprises one of:

a brake motor; and a non-back-drivable gear box coupled between the brake motor and the at least one brake pad, the gear box having a worm driven by the brake motor and a worm wheel engaging the worm;

the at least one brake pad including a pair of brake pads, including: a first movable brake pad on a first side of the rotor, and a second stationary brake pad on a second side of the rotor and carried by a frame of the locking mechanism;

the rotor being slidably positioned on the drive shaft and the rotor being keyed radially to the drive shaft with the rotor and the drive shaft rotating together; or a cam engaging the at least one brake pad and having a lobe with a greater radial length configured to press the brake pad towards the rotor, and a heel with a lesser radial length configured to release the brake pad from the rotor, and a brake motor coupled to and selectively turning the cam.

27. The foot and ankle prosthesis of claim 23, wherein the locking mechanism engages the drive motor under speed and torque; and wherein the locking mechanism engages the drive motor under load with the foot and ankle prosthesis transitioning between active and passive modes without waiting for the locking mechanism to lock.

* * * * *